US 6,562,069 B2

(12) United States Patent
Cai et al.

(10) Patent No.: US 6,562,069 B2
(45) Date of Patent: May 13, 2003

(54) POLYMER LEAFLET DESIGNS FOR MEDICAL DEVICES (75) Inventors: Chad Q. Cai, Woodbury, MN (US); Steven D. Kruse, Bloomington, MN (US); James L. Kurk, Anoka, MN (US); Yi-Ren Woo, Woodbury, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 13 days.

(21) Appl. No.: 09/955,703

(22) Filed: Sep. 19, 2001

(65) Prior Publication Data
US 2003/0055496 A1 Mar. 20, 2003

(51) Int. Cl.$^7$ .................................................. A61F 2/06
(52) U.S. Cl. ...................................... 623/2.12; 623/2.17
(58) Field of Search ...................... 623/2.12, 2.14–2.19, 623/2.1, 1.24

(56) References Cited

U.S. PATENT DOCUMENTS

| 3,717,883 | A | | 2/1973 | Mosher |
| 3,861,416 | A | | 1/1975 | Wichterle |
| 4,218,782 | A | | 8/1980 | Rygg |
| 4,222,126 | A | | 9/1980 | Boretos et al. |
| 4,265,694 | A | | 5/1981 | Boretos et al. |
| 4,291,420 | A | * | 9/1981 | Reul ......................... 623/2.12 |
| 4,364,127 | A | * | 12/1982 | Pierce et al. ............... 623/2.12 |
| 4,417,360 | A | | 11/1983 | Moasser |
| 4,451,936 | A | | 6/1984 | Carpentier et al. |
| 4,544,599 | A | | 10/1985 | Buttazzoni |
| 4,556,996 | A | | 12/1985 | Wallace |
| 4,624,822 | A | | 11/1986 | Arru et al. |
| 4,731,074 | A | * | 3/1988 | Rousseau et al. .......... 623/2.12 |
| 4,778,461 | A | | 10/1988 | Pietsch et al. |
| 4,781,716 | A | | 11/1988 | Richelsoph |
| 4,834,747 | A | | 5/1989 | Gogolewski |
| 4,888,009 | A | | 12/1989 | Lederman et al. |

(List continued on next page.)

FOREIGN PATENT DOCUMENTS

| EP | 0 331 345 A2 | 9/1989 |
| EP | 0 632 711 B1 | 12/1997 |
| EP | 0 850 607 A1 | 7/1998 |
| RU | 316446 | 10/1971 |
| RU | 1144216 A | 10/1987 |
| WO | WO 98/32400 | 7/1998 |
| WO | WO 01/05334 A1 | 1/2001 |
| WO | WO 02/24119 A1 | 3/2002 |

OTHER PUBLICATIONS

Kurk et al., "Polymer Valve Prosthesis by Dip Coating", U.S. patent application No. 09/724,007, filed Nov. 28, 2000.

Primary Examiner—David H. Willse
Assistant Examiner—Suzette Jackson
(74) Attorney, Agent, or Firm—Altera Law Group, LLC (57) ABSTRACT Valved prostheses include a support structure and a plurality of flexible polymer leaflets connected to the support structure, in which the leaflets have an improved structural design. The support structure has a plurality of commissure supports and scallops between the commissure supports. Generally, the flexible polymer leaflets project away from the support structure at an attachment edge where the leaflets connect to the support structure. In particular embodiments, the leaflets at the attachment edge are at an angle from about 5 degrees to about 85 degrees relative to a plane normal to the valve axis. In some embodiments, the flexible polymer leaflets having a coaptation depth from about 0.3 times the valve radius to about 0.8 times the valve radius. In further embodiments, the flexible polymer leaflets form a valve with a valve height from about one times the valve radius to about 2 times the valve radius and have leaflet lengths at least about 1 millimeter greater than the valve radius.

32 Claims, 8 Drawing Sheets

U.S. PATENT DOCUMENTS

| | | |
|---|---|---|
| 4,904,254 A | 2/1990 | Lane |
| 5,024,232 A | 6/1991 | Smid et al. |
| 5,078,739 A | 1/1992 | Martin |
| 5,094,661 A | 3/1992 | Levy et al. |
| 5,094,876 A | 3/1992 | Goldberg et al. |
| 5,116,564 A | 5/1992 | Jansen et al. |
| 5,139,515 A | 8/1992 | Robicsek |
| 5,147,389 A | 9/1992 | Lane |
| 5,163,960 A | 11/1992 | Bonutti |
| 5,358,518 A | 10/1994 | Camilli |
| 5,376,113 A | 12/1994 | Jansen et al. |
| 5,415,667 A | 5/1995 | Frater |
| 5,449,385 A | 9/1995 | Religa et al. |
| 5,476,471 A | 12/1995 | Shifrin et al. |
| 5,480,424 A | 1/1996 | Cox |
| 5,500,014 A | 3/1996 | Quijano et al. |
| 5,554,184 A | 9/1996 | Machiraju |
| 5,562,729 A | 10/1996 | Purdy et al. |
| 5,605,693 A | 2/1997 | Seare, Jr. |
| 5,683,451 A | 11/1997 | Lenker et al. |
| 5,766,247 A | 6/1998 | Aoki et al. |
| 5,766,710 A | 6/1998 | Turnlund et al. |
| 5,776,190 A | 7/1998 | Jarvik |
| 6,139,575 A | 10/2000 | Shu et al. |
| 6,171,335 B1 * | 1/2001 | Wheatley et al. .......... 623/2.17 |
| 6,174,331 B1 | 1/2001 | Moe et al. |
| 6,283,994 B1 * | 9/2001 | Moe et al. .................... 62/2.12 |
| 6,338,740 B1 * | 1/2002 | Carpentier ................. 623/2.13 |
| 6,395,025 B1 * | 5/2002 | Fordenbacher et al. .... 623/2.28 |
| 6,454,798 B1 * | 9/2002 | Moe .......................... 623/2.12 |
| 6,478,819 B2 * | 11/2002 | Moe .......................... 623/2.18 |

* cited by examiner

POLYMER LEAFLET DESIGNS FOR MEDICAL DEVICES

BACKGROUND OF THE INVENTION

The invention relates to valved prostheses having flexible polymer leaflets. The invention further relates to improved leaflet designs.

Physicians use a variety of prostheses to correct problems associated with the cardiovascular system, especially the heart. For example, the ability to replace or repair diseased heart valves with prosthetic devices has provided surgeons with a method of treating heart valve deficiencies due to disease and congenital defects. A typical procedure involves removal of the native valve and surgical replacement with a prosthetic heart valve.

Prosthetic heart valve leaflets or occluders perform the function of opening and closing to regulate the blood flow through the heart valve. Typically, heart valve leaflets must either pivot or flex with each cycle of the heart to open and close the valve. Heart valves function as check valves, which open for flow in one direction and close in response to pressure differentials to limit reverse flow.

Prostheses can be constructed from natural materials such as tissue, synthetic materials or a combination thereof. Prostheses formed from purely synthetic materials can be manufactured, for example, from biocompatible metals, ceramics, carbon materials, such as graphite, polymers, such as polyester, and combinations thereof. Heart valve prostheses with purely synthetic materials can be manufactured with rigid occluders (leaflets) that pivot to open and close the valve, or flexible leaflets that flex to open and close the valve.

Although mechanical heart valves with rigid pivoting occluders have the advantage of proven durability through decades of use, they are associated with blood clotting on or around the prosthetic valve and thromboembolism. Blood clotting can lead to acute or subacute dysfunction of the valve. For this reason, patients with mechanical heart valves remain on anticoagulants for as long as the valve remains implanted. Anticoagulants have associated risks and cannot be taken safely by certain individuals.

Heart valve prostheses with flexible leaflets can be constructed with tissue leaflets or polymer leaflets. In prostheses with flexible leaflets, the leaflets are generally designed to approximate natural leaflet function. While the leaflets are flexible, they must have a well defined and stable configuration to properly open and close the valve at each cycle in response to pressure differentials. Also, the leaflets should be durable to provide stable performance over many years of use.

Unlike mechanical valves, tissue based bioprostheses may not require the long term use of anticoagulants due to a lower incidence of thromboembolism. While tissue leaflets have desired flexibility and acceptable hemodynamic performance, tissue leaflets can calcify after implantation, which may result in loss of flexibility or improper closure and/or opening of the valve.

Valve prostheses with polymer leaflets have the potential to overcome the shortcomings of both tissue and mechanical valve designs. The polymers incorporated into heart valve prostheses should provide long term stable function to be suitable alternatives for tissue leaflets or mechanical leaflets.

SUMMARY OF THE INVENTION

In a first aspect, the invention pertains to a valved prosthesis including a support structure and a plurality of flexible polymer leaflets connected to the support structure. The support structure has a plurality of commissure supports and scallops between the commissure supports, and the valve has a relaxed state with a lumen that is at least 10 percent of the full open lumen. The flexible polymer leaflets connect to an attachment edge of the leaflet at an angle. In particular embodiments, at a point along the scallops closest to the inflow edge, the flexible polymer leaflets connect to the support structure at an angle toward the inflow edge from about 5 degrees to about 85 degrees relative to a plane normal to the valve axis.

In another aspect, the invention pertains to a valved prosthesis comprising a support structure and at least three flexible polymer leaflets connected to the support structure. The support structure has a plurality of commissure supports and scallops between the commissure supports. The flexible polymer leaflets have a coaptation depth from about 0.3 times the valve radius to about 0.8 times the valve radius.

In another aspect, the invention pertains to a valved prosthesis comprising a support structure and a plurality of flexible polymer leaflets. The support structure has a plurality of commissure supports and scallops between the commissure supports. The flexible polymer leaflets from a valve with a valve height from about one times the valve radius to about 2 times the valve us. The flexible polymer leaflets have leaflet lengths at least about 1 millimeter greater than the valve height.

DETAILED DESCRIPTION OF THE ILLUSTRATIVE EMBODIMENTS

Improved polymer leaflet structures have been designed for valved prostheses. To perform at a satisfactory level over an extended period of time, the stresses in the polymer leaflet should be reduced over the valve cycle of opening and closing. Several structural features of the polymer leaflet can be introduced to reduce the stresses within the leaflets during the cycling and improve hemodynamic performance and leaflet coaptation. The performance criteria for polymer leaflets are stringent since the leaflets must be thin enough to have suitable flexibility and good closure, while maintaining mechanical performance over years of continuous use. In particular, the leaflets should have high tear resistance and wear resistance for long term performance. Improved polymer leaflet designs with specific features are presented for valves that have a relaxed state of the leaflets resulting in a fully open valve, a partially open valve or a fully closed valve.

The improved polymer leaflets can be used in valved prostheses, especially heart valve prostheses. Damaged or diseased natural heart valves can be replaced with valved prostheses to restore valve function. Heart valve prostheses of interest have leaflets formed from polymers. The polymers form flexible leaflets similar to native tissue leaflets. The polymer heart valve prosthesis can be designed as a replacement for any heart valve, i.e., an aortic valve, a mitral valve, a tricuspid valve, or a pulmonary valve. In addition, the improved polymer valve prostheses can be used for the replacement of vascular valves. The patient can be an animal, especially a mammal, and preferably is a human.

In a valve with polymer leaflets, the leaflets are supported by a support structure that includes commissure supports and scallops between the commissure supports. The support structure of the valve may include a sewing cuff or the like for attachment of the valve to the patient's annulus, to other components of a medical device, or anatomical structure.

In some embodiments, the support structure includes a rigid component that maintains the leaflet function of the valve against the forces opening and closing the valve. Valves with a rigid support structure are termed stented valves, and the rigid support is called a stent. The stent provides a scaffolding for the leaflets. The stent includes commissure supports that support the ends of the free edge of the leaflets. Commissure supports may or may not extend beyond the attachment points of the leaflet in the flow direction. Scallops, which support the attached edges of the leaflets, extend between the commissure supports. The stent generally is sufficiently rigid such that only the base of the stent is attached to the patient or other device. As a particular example, heart valve stents are used to support leaflet components within a prosthetic heart valve.

In alternative embodiments, the support structure is not sufficiently rigid to maintain the leaflet fiction of the valve against the forces opening and closing the valve. In these embodiments, the valve is termed stentless. In a stentless valve, the support structure also has commissure supports at which the free edge of the leaflet connects with the support structure, and scallops which support the attached edge of the leaflets. However, in the stentless valve, the support structure is less rigid such that both edges of the support structure, i.e., the inflow edge and the outflow edge, must be secured such as by suturing or other fastening approach to other anatomical structures, such as the wall of a blood vessel, or to other device structures, to prevent the valve from collapsing against the fluid pressure. The support structure can include the same polymer as used in the leaflets or other flexible material or materials in a generally cylindrical configuration that defines the commissure supports and the scallops or other suitable interface that hold the attached edges of the leaflet.

The valve includes a plurality of leaflets. Preferred valves have three leaflets. The polymer leaflets are configured to flex in response to changes in blood flow. The leaflets flex between the open and closed configurations according to the constraints provided by the attached edge. In particular, preferred embodiments of the valves function as one way check valves that open to allow flow in a desired direction and close in response to pressure differentials to limit reverse flow. Thus, when blood is flowing downstream, the leaflets fully open to allow for flow through the valve. In the open position, the free edges of the polymer leaflets form the downstream opening of the valve and generally do not significantly resist forward blood flow.

When the valve closes in response to pressure differentials, the free edges of adjacent leaflets contact in a closed position with the leaflets extending across the lumen of the valve. The contact of adjacent leaflet free edges across the lumen of the valve eliminates or greatly reduces back flow through the valve. The contacting portion of the leaflets is referred to as the coaptation region.

The leaflets are formed from a film of flexible polymer, such that the film can flex in response to blood flow to open and close the valve. Suitable polymers are biocompatible, in that they are non-toxic, non-carcinogenic and do not induce hemolysis or an immunological response. Heart valve prostheses formed from polymers generally are non-thrombogenic. Relevant mechanical properties of polymers include, for example, stiffness, strength, creep, hardness, fatigue resistance and tear resistance. Preferred polymers are durable in that they do not significantly lose their flexibility and do not significantly lose their mechanical strength following many years of use.

The relaxed state of the leaflets corresponds to the leaflet configuration when no forces are applied to the leaflets. The relaxed state of the leaflets is determined at the formation of the valve. This relaxed state can correspond to an almost closed leaflet configuration, a fully open leaflet configuration or a partially open leaflet configuration. Each selection of the relaxed state of the polymer leaflets has particular advantages. Valves with relaxed leaflets in a fully open configuration provide optimal hemodynamics. Valves with relaxed leaflets in an almost closed configuration reduce fully closed stresses, such that the valves may last longer and are less likely to calcify. Valves with relaxed leaflets in a partially open configuration reduce bending stresses during valve cycling.

The design of the polymer leaflets and their attachment to the support structure affects the mechanical performance of the valve, including the stresses on the leaflets in operation. Specifically, the size and shape of the leaflets can be designed to reduce leaflet stresses for improved mechanical performance, a reduction of wear over the life of the valve and improve hemodynamics and coaptation. Particular improvements may depend on the relaxed state of the leaflets.

For valves with three or more leaflets, the valve orifice generally is related to the circle that is obtained from a least squares fit of all the commissure supports when they are projected onto the commissure plane. The commissure plane is obtained by a least squares fit of a planar surface relating to the commissure supports, which are the attachment points of the free edges of the leaflets with the support structure. For three commissure supports, the commissure plane is uniquely defined without fitting by the commissure supports. For valves with two commissure supports, the commissure plane is the plane perpendicular to the valve axis with the least squares distance to the commissure supports. The valve radius is the radius of the valve orifice. The valve axis is the axis that goes through the center of the valve normal to the valve orifice. The valve also has an orifice opening at the inflow edge related to the inner diameter of the support structure at the inflow edge. The orifice opening at the inflow edge can be approximately the same as the orifice opening at the outflow edge or slightly larger or smaller due to taper of the support structure.

The coaptation point of the leaflets is the lowest point where all the leaflets meet when the valve is subject to a minimal amount of pressure that brings the leaflets to their closed position. The coaptation depth is the shortest distance from the coaptation point to the commissure plane. In preferred embodiments, the coaptation depth is non-zero such that the free edge makes a non-zero angle with respect to the commissure plane since the leaflets then transfer the pressure load more effectively to the stent post.

The valve height is the longest distance along the direction of the valve axis between the commissure plane and the lowest point on the attachment edges. In some preferred embodiments, valve height is between about one and two times the valve radius. The leaflet length of a leaflet is the distance from the center of the free edge to the middle of the corresponding scallop where the leaflet is attached to the support structure. In preferred embodiments with three or more leaflets, the leaflet length is greater than the shortest distance from the attachment edge in the center of the scallop to the coaptation point.

As noted above, the leaflets have an attachment edge along the scallops of the support structure between two adjacent commissures. The attachment edges of two adjacent leaflets end at the same commissure. Preferred leaflet structures have a portion of the leaflet extending toward the inflow edge on the inflow side of the plane through the lowest point of the attachment edge when the leaflets are in a closed position under pressure. In these embodiments, the portion of the polymer leaflets on the inflow side relative to the attachment edge have a curvature such that the free edge of the leaflet is oriented generally toward the outflow edge of the valve. The curved portion of the leaflet distributes a partial load to the bottom part of the scallops due to the downward leaflet attachment when the leaflet is under closing pressure.

This structure is described further below with respect to FIG. 8. This preferred structure reduces the total load borne by the commissure areas at which the leaflet free edge attaches to the support structure. The commissure area is the point of highest stress. When the valve is oriented in a position with the valve axis being vertical and the inflow edge is pointed downward, the attachment angle is the angle between a tangent line of the leaflet curve at the attachment point and a horizontal line in the leaflet cross section plane normal to the attachment edge at a particular attachment point. The attachment angle reaches its maximum at the lowest position of the scallops and decreases along the attachment edge, vanishing at the commissure posts. In the closed position, the leaflet can form a desired attachment angle with a smooth "bowing" profile to distribute stresses effectively.

The fully open position is defined as the leaflet position where the projected opening area on the commissure plane encompassed by the leaflet free edges reaches its maximum during a typical heart beat cycle. A typical heart beat cycle is conventionally considered to correspond to an average output of 5 liters per minute, an average of 70 beats per minute and an average aortic pressure of 100 mmHg. Approved test conditions for heart valve prostheses are described further in ISO 5840:1996 publication (International Organization For Standardization), incorporated herein by reference. This maximum area is the full open lumen. The full open lumen can be larger than the valve orifice.

Leaflet designs involving a relaxed state intermediate between the fully open and closed configurations may offer advantages relative to either valves that are approximately open or approximately closed in the relaxed state. Valves with leaflets in an intermediate relaxed state generally have relaxed leaflets with a lumen that is between about 50 percent and about 80 percent of the fully open lumen. With a relaxed state that is intermediate between the fully open and fully closed configurations, the magnitude of deviations of the leaflet structure from the relaxed state is reduced relative to leaflet designs with a relaxed state close to the fully open or fully closed configurations. Thus, bending stresses over the opening and closing cycle may be reduced. In contrast, the valves with a relaxed state close to the full open lumen provide particularly good flow through the open valve but may need to bend significantly from the relaxed state to close the valve. Similarly, valves with a relaxed state near the closed configuration have reduced stresses when closed but may need to bend significantly to open to the full lumen to provide flow through the valve.

Generally, polymer leaflets can be formed by a variety of casting and molding processes. In preferred embodiments, the leaflets are formed by dip coating a mandrel. The mandrel is machined to generate the desired contours for the leaflets. The surface of the mandrel forms a surface to which the leaflets conform when a thin polymer layer is applied to the mandrel, generally by dip coating. As removed from the mandrel, the leaflet is in its relaxed state with no applied stress or tension. Thus, improved leaflet features relating to size and shape are reflected in the contours on the mandrel surface.

In some preferred embodiments, the leaflets are formed directly in association with the corresponding support structure, either a stent or a flexible support structure. In these embodiments, the support structure is coated with the polymer along with the mandrel during the coating process. Flexible support structures can be formed during the dip coating process itself. By associating the support structure with the leaflets while forming the leaflets, an additional step involving the association of the polymer leaflets with a support structure can be avoided.

If necessary, the polymer structure removed from the mandrel after forming the leaflets can be trimmed and/or secured to the support structure. A sewing ring may be attached to the base of the polymer structure or a support structure to provide for attachment/implantation of the valve. The valve can be implanted as a prosthesis, attached to additional structure, such as a conduit, for implantation as a prosthesis or connected to additional structure to form a medical device that operates outside of a patient.

Valved Prostheses

The improved polymer leaflets can be used in valved prostheses. In particular, the leaflets can be used in artificial hearts, heart valve prostheses, valved vascular prostheses or left ventricular assist devices. The polymer leaflets open and close to control flow through the valve.

Heart valve prostheses with polymer leaflets are suitable for the replacement of damaged or diseased native heart valves. Mammalian hearts have four major valves. With appropriate sizing and attachment, the polymer valves of the present invention are suitable for replacement of any of the heart valves. Polymer heart valve prostheses for replacement of the mitral and tricuspid valves generally include rigid stents.

While the embodiments of the heart valve prosthesis shown in the figures below have three polymer leaflets, heart valve prostheses can be constructed with different numbers of polymer leaflets, such as two leaflets, four leaflets or more than four leaflets. However, as noted appropriately, some preferred parameters are most suitable for valves with three or more leaflets. The prosthesis may or may not have the same number of leaflets as the natural valve that it is used to replace.

Mammalian veins include valves that assist with blood circulation by limiting the amount of back flow in the veins. Veins collect blood from capillaries and are responsible for returning blood to the heart. Generally, vascular valves are replaced as part of a vascular graft with sections of conduit.

Figure 1:
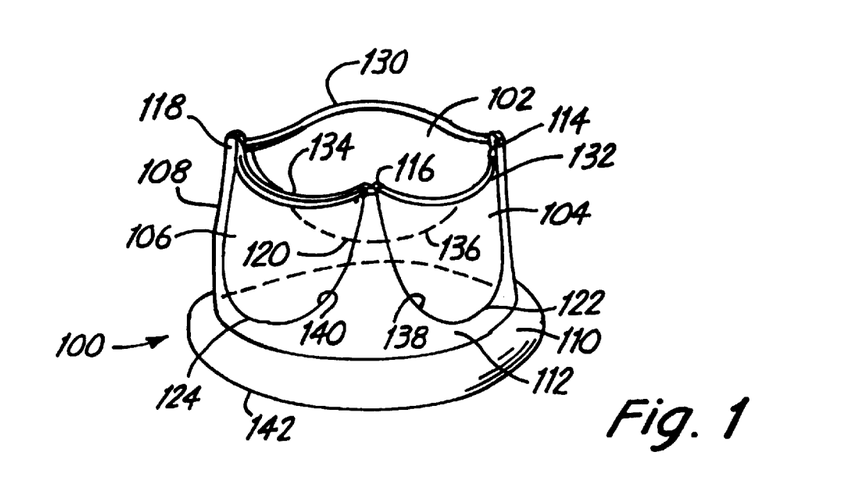
FIG. 1 is a perspective view of a heart valve prosthesis with the leaflets in their relaxed state, wherein the valve is approximately fully open.

An embodiment of a heart valve prosthesis with flexible polymer leaflets is shown in FIG. 1 in its relaxed state with approximately fully open leaflets. If the leaflets are fully open in their relaxed state, the forces applied by fluid flowing from the inflow edge through the valve would not alter the leaflet position significantly. To be considered approximately fully open in its relaxed state, the relaxed leaflets provide an opening that is at least about 90% of the full valve lumen. In some embodiments, the approximately fully open valve has relaxed leaflets at least about 95% open and in other embodiment at least about 98% open.

The fully open leaflets are obtained when the projected opening area on the commissure plane encompassed by the leaflet free edges reaches its maximum during a typical heart beat cycle. The fully open leaflets form the open lumen of the outflow edge of the valve, i.e., the full valve lumen. The open lumen of the outflow edge of the valve may not be the same as the open lumen at the inflow edge of the valve. The open lumen at the inflow edge of the valve is determined by dimensions of a rigid stent or by the patient's annulus for non-rigid support structures. The open lumen at the outflow edge can be larger or smaller than the open lumen at the inflow edge due to taper of the support structure.

Heart valve prosthesis 100 includes leaflets 102, 104, 106, support structure/stent 108 and sewing ring 110. Support structure/stent 108 can be relatively rigid, such that the support structure functions as a stent to maintain leaflet function with attachment to the patient at base 112 of support structure 108. Alternatively, support structure 108 can be less rigid as part of a stentless valve, with support structure 108 being secured to other anatomical structures or other devices to maintain the leaflet function.

Support structure/stent 108 includes commissure supports 114, 116, 118 and scallops 120, 122, 124 between the commissure supports. Free edges 130, 132, 134 of leaflets 102, 104, 106, respectively, join at the commissure supports 114, 116, 118. Attached edges 136, 138, 140 of leaflets 102, 104, 106 also attach to the support structure along scallops 120, 122, 124. If support structure 108 is not rigid, support structure 108 should be secured to anatomical structures of other devices sufficiently to maintain proper leaflet function. Base 112 of support structure 108 generally is a cylindrical ring that forms the opening into the valve at the inflow or proximal end 142 of valve 100.

Sewing ring 110 generally extends from base 112 of support structure 108, although some embodiments may not require a sewing ring, especially with flexible support structures. Sewing ring 110 facilitates the attachment of the heart valve prosthesis to the patient or to other components of a device. Suture, staples and/or other fastening mechanisms are passed through the sewing cuff to secure sewing cuff 110 to the patient's tissue annulus, to other anatomical structure, to a conduit prosthesis or to other portions of a medical device.

Figure 2:
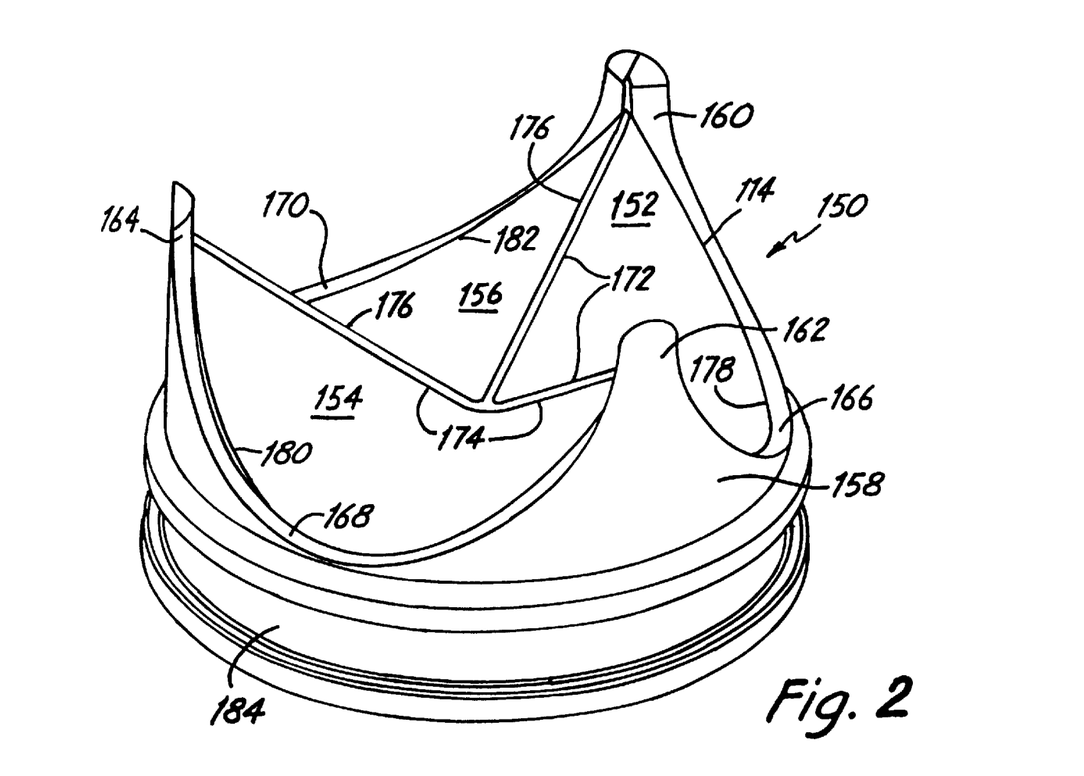
FIG. 2 is a perspective view of a heart valve prosthesis with the leaflets in their relaxed state, with approximately fully closed leaflets.

An embodiment of a heart valve prosthesis 150 with flexible polymer leaflets is shown in FIG. 2 having a relaxed state with approximately fully closed leaflets. Approximately fully closed leaflets block generally at least about 90%, in other embodiments at least about 98%, and in other embodiments, at least about 99% of the full open lumen. In other words, the open area between the relaxed leaflets in these embodiments is no more than about 10% of the full open lumen. Heart valve prosthesis 150 includes leaflets 152, 154, 156 and support structure/stent 158. Again, support structure/stent 158 can be relatively rigid as part of a stented valve, or less rigid as part of a stentless valve.

Support structure/stent 158 includes commissure supports 160, 162, 164 and scallops 166, 168, 170 between the commissure supports. Free edges 172, 174, 176 of leaflets 152, 154, 156, respectively, join support structure/stent 158 at the commissure supports 160, 162, 164. Attached edges 178, 180, 182 of leaflets 152, 154, 156 also attach to the support structure along scallops 166, 168, 170. Base 184 of support structure 158 generally is a cylindrical ring that forms the opening into the valve at the upstream or proximal end of the valve.

Partially open leaflets in their relaxed state have an opening between the fully closed configuration and the fully open configuration, i.e. a relaxed opening between about 10% and about 90% of the full open lumen. In preferred embodiments, the relaxed leaflets have an opening between about 50% and about 90%, and in other embodiments, between about 60% and about 80% of the full open lumen of the valve. While valves with relaxed leaflets which open between about 10% and about 49% of the full open lumen can advantageously incorporate some of the features of the present invention, partially open leaflets with a relaxed state in the preferred ranges are particularly advantageous with respect to reducing bending stresses The design of leaflets with a partially open leaflet configuration does not necessarily approximate one of the transient points of the leaflets during the valve cycle. A selected partially open configuration may not correspond to any position of the leaflets in the valve cycle due to the constantly varying pressure load both in magnitude and distribution on valve leaflets that determines leaflet shape between the open and closed position at any instance.

Figure 3A:
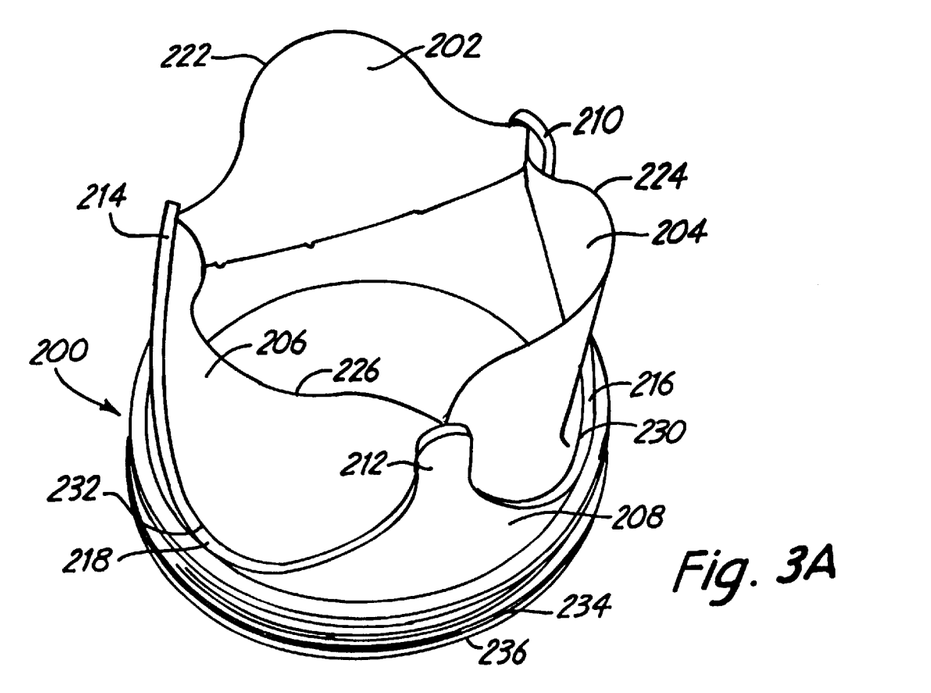
FIG. 3A is a perspective view of a heart valve prosthesis with the leaflets in their relaxed state, wherein the valve lumen is about 90% open.
Figure 3B:
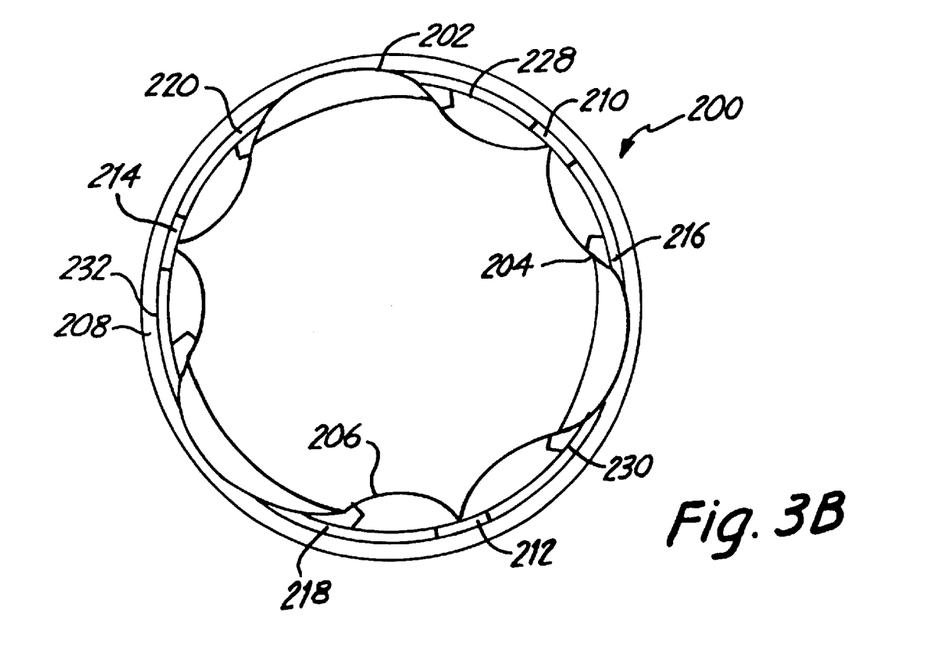
FIG. 3B is a top view of the valve of FIG. 3A.

An embodiment of a heart valve prosthesis 200 with flexible polymer leaflets is shown in FIGS. 3A and 3B having a relaxed state with about 90% of the full valve lumen. Heart valve prosthesis 200 includes leaflets 202, 204, 206 and support structure/stent 208. Again, support structure/stent 208 can be relatively rigid as part of a stented valve, or less rigid as part of a stentless valve.

Support structure/stent 208 includes commissure supports 210, 212, 214 and scallops 216, 218, 220 between the commissure supports. Free edges 222, 224, 226 of leaflets 202, 204, 206, respectively, join support structure/stent 208 at the commissure supports 210, 212, 214. Attached edges 228, 230, 232 of leaflets 202, 204, 206 also secure to the support structure along scallops 216, 218, 220. The base 234 of support structure 208 generally is a cylindrical ring that forms the opening into the valve at the inflow or proximal end 236 of the valve.

Figure 4A:
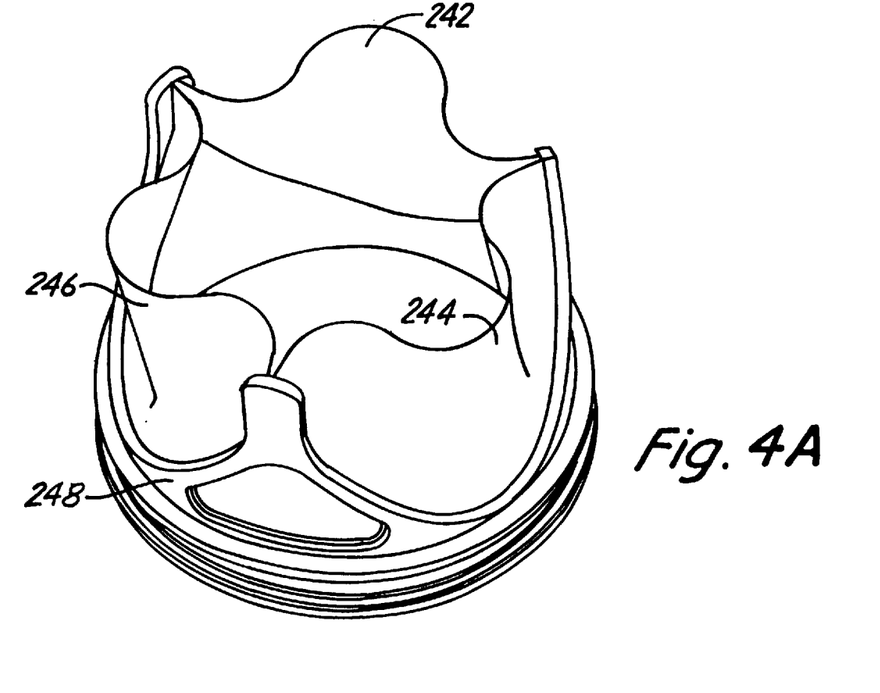
FIG. 4A is a perspective view of a heart valve prosthesis with the leaflets in their relaxed state, wherein the valve lumen is about 70% open.
Figure 4B:
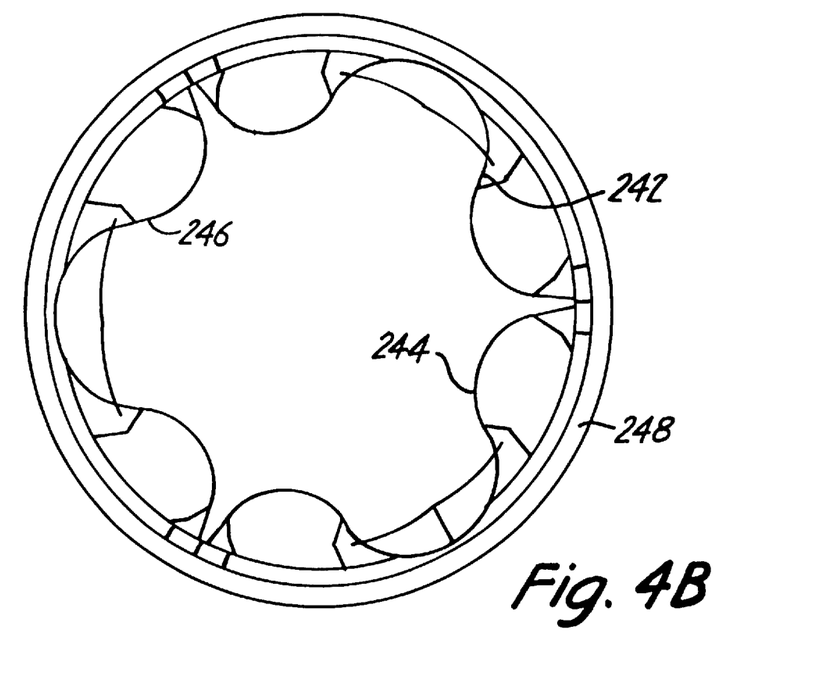
FIG. 4B is a top view of the valve of FIG. 4A.
Figure 5A:
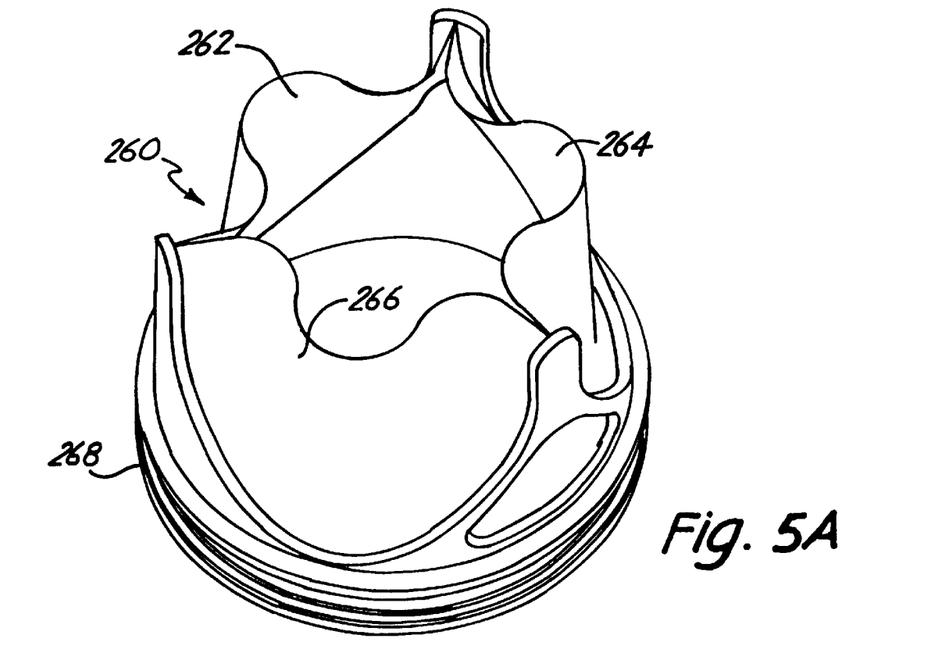
FIG. 5A is a perspective view of a heart valve prosthesis with the leaflets in their relaxed state, wherein the valve lumen is about 50% open.
Figure 5B:
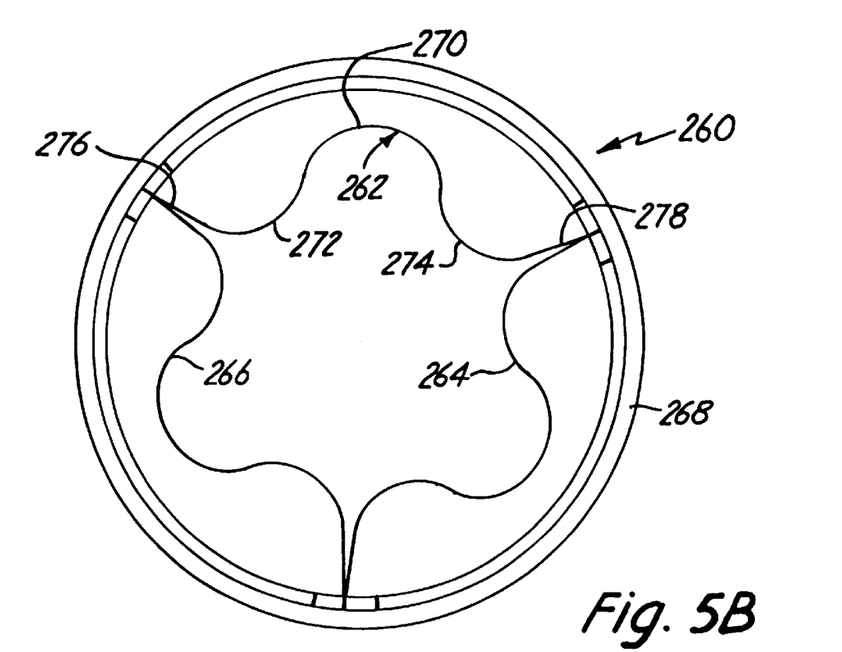
FIG. 5B is a top view of the valve of FIG. 5A.

Similarly, an embodiment of a heart valve prosthesis 240 with flexible polymer leaflets is shown in FIGS. 4A and 4B having a relaxed state with about 70% of the full valve lumen. Heart valve prosthesis 240 includes leaflets 242, 244, 246 and support structure/stent 248. In addition, an embodiment of a heart valve prosthesis 260 with flexible polymer leaflets is shown in FIGS. 5A and 5B having a relaxed state with about 50% of the full valve lumen. Heart valve prosthesis 260 includes leaflets 262, 264, 266 and support structure/stent 268.

Top views of valves with partially open leaflets in their relaxed state at about 90%, 70% and 50% of the valve lumen are shown, respectively, in FIGS. 3B, 4B, 5B. These top views provide a clear perspective of the ranges of the open lumen corresponding to relaxed leaflet configurations for preferred versions of the valves with partially open valve leaflets.

While the relaxed leaflet configuration may not correspond to leaflet positions during the valve cycle, a suitable contour to represent the partially open configuration can be selected. For the partially open valve, the free edge of the leaflet forms a smooth contour about its center point. As shown in FIG. 5B, a contour for leaflet 262 can be considered to have five sections, a center curved section 270, a side curved section 272, 274 on each side of the center curved section and a connecting section 276, 278 on each side of the leaflet. Center curved section 270 forms the central part of the contour with the center of the curvature on the inside of the valve open area. Side curved sections 272, 274 connect to center curved section 270 through an inflection point on either side of center curved section 270. Connecting sections 276, 278 connect side curved sections 272, 274 to the attachment point on the valve support structure on either side of the free edge contour.

For partially open valves generally, the magnitude of the radii of curvature of the side curved section is generally within about 30% of the curvature of the center curved section and preferably within 15% of the curvature of the center-curved section. The connecting section is approximately straight and has a length approximately equal to a percentage of the free edge length of the leaflet calculated by ((100−%open)/5)%. For example, a 70% open valve would have a connecting section with a length of ((100−70)/5)% or 6% of the free edge length.

The embodiments with a partially open configuration have the advantage that the extremes in the stresses as the valve cycles between the fully open and fully closed configurations are reduced. This reduction in the maximum bending stresses results from a reduction in the movement of the leaflets relative to the relaxed state of the leaflets over the cycle of the valve opening and closing. Since the leaflets have a relaxed contour between the fully open and fully closed configurations, the leaflets deform less in moving from the fully open to the fully closed positions.

In prostheses, flexible leaflets replace native leaflet function. While these leaflets are flexible, they must have a well defined and stable configuration to properly close at each cycle to prevent back flow. Also, the leaflets should be durable to provide stable performance over many years of use.

The design of the polymer leaflets can affect their performance in a valve. In particular, the shape and size of the leaflet in its relaxed state will define the shape and configuration of the leaflet at points in the opening and closing cycle at any given pressure load. Thus, by constructing the leaflets in their relaxed state as described herein, the structure of the polymer leaflet can be selected to reduce stresses through the opening and closing cycle. In general, the valve is subjected to maximum stress in its closed position, regardless of the relaxed state of the leaflets.

Four parameters relating to leaflet shape and size particularly influence the leaflet stresses. These parameters are the coaptation depth, valve height, leaflet length and the attachment angle. These parameters apply to leaflets regardless of their relaxed configuration.

The valve generally has the greatest stresses in the closed configuration. Selection of the coaptation depth in the closed valve can be used to reduce leaflet stresses. The coaptation depth is the shortest distance from the coaptation point to the commissure plane. Assuming that the three leaflets have identical dimensions and are symmetrically located about the axis, which they are in preferred embodiments, the three leaflets meet in the center of the valve lumen when the valve is closed. The configuration of the closed leaflet is a function of the coaptation depth, assuming that the leaflet is sufficiently flexible. If the free edge of the polymer leaflet has a length of approximately twice the radius of the valve, the leaflets in the closed valve generally meet with their free edges all approximately in a plane with a zero coaptation depth.

Reduced stress can be obtained by having a non-zero coaptation depth. In other words, these embodiments have a polymer leaflet free edge with a length greater than twice the valve radius. Such lengths of the leaflet free edges results in coapting leaflets with free edges that meet on the inflow side below the plane formed by the attachment points of the leaflets on the commissure supports. While a non-zero coaptation depth is preferred, the coaptation depth generally is less than 0.8 times the valve radius, and preferably from about 0.3 times the radius to about 0.6 times the valve radius. Generally, a larger coaptation depth yields a larger angle between the free edge of the leaflet and the commissure plane. An angle larger than zero is desirable because the leaflet then transfers the pressure load more effectively to the commissure support. For valves with a straight leaflet free edge, the coaptation depth determines the length of the leaflet free edge and the angle between the leaflet free edge and the commissure plane. The angle of the free edge of the leaflet at the commissure support can be less than about 39° and in other embodiments from about 16.7° to about 35°.

Figure 6:
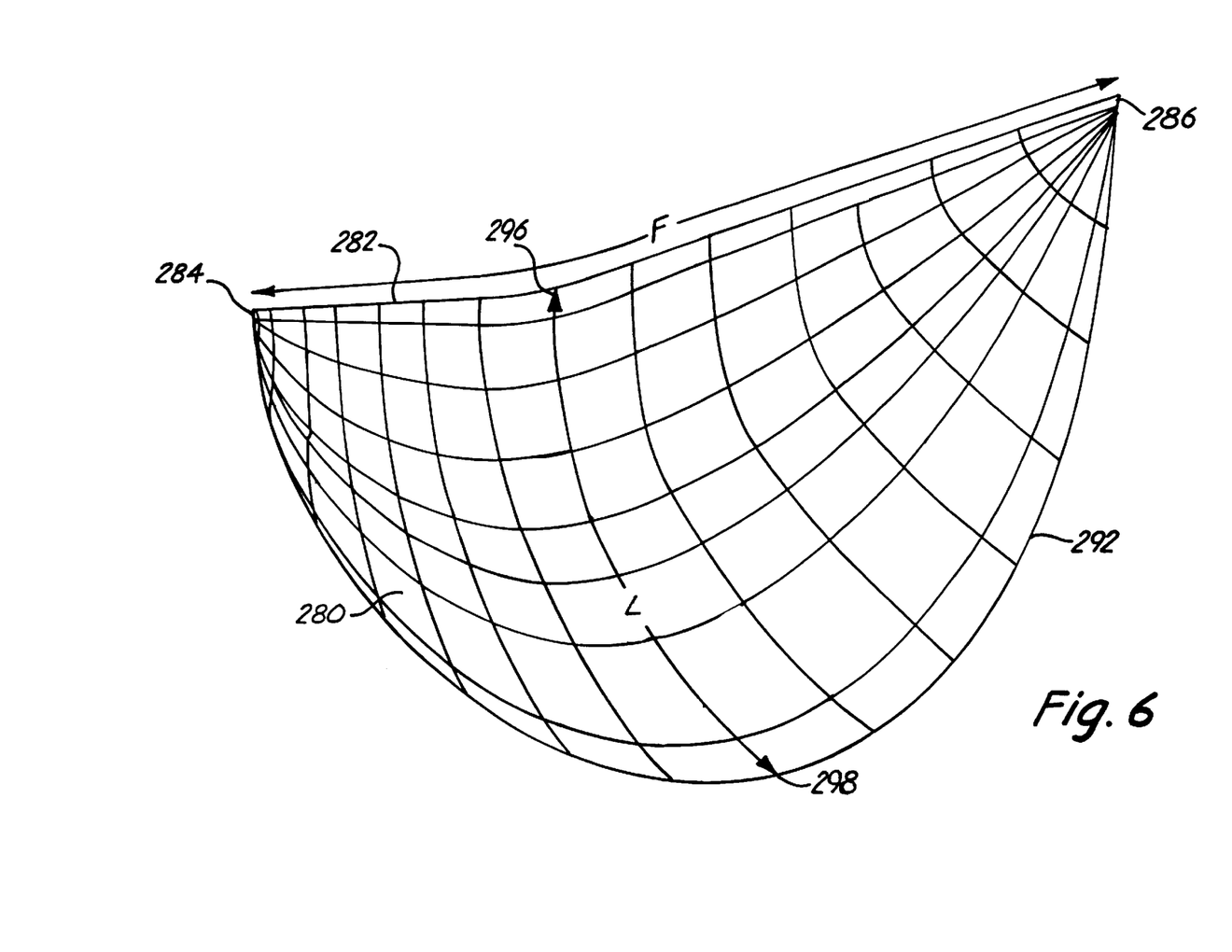
FIG. 6 is a perspective view of a polymer leaflet separated from the prosthesis in an orientation corresponding to an open configuration wherein certain dimensions of the leaflet are marked.
Figure 7:
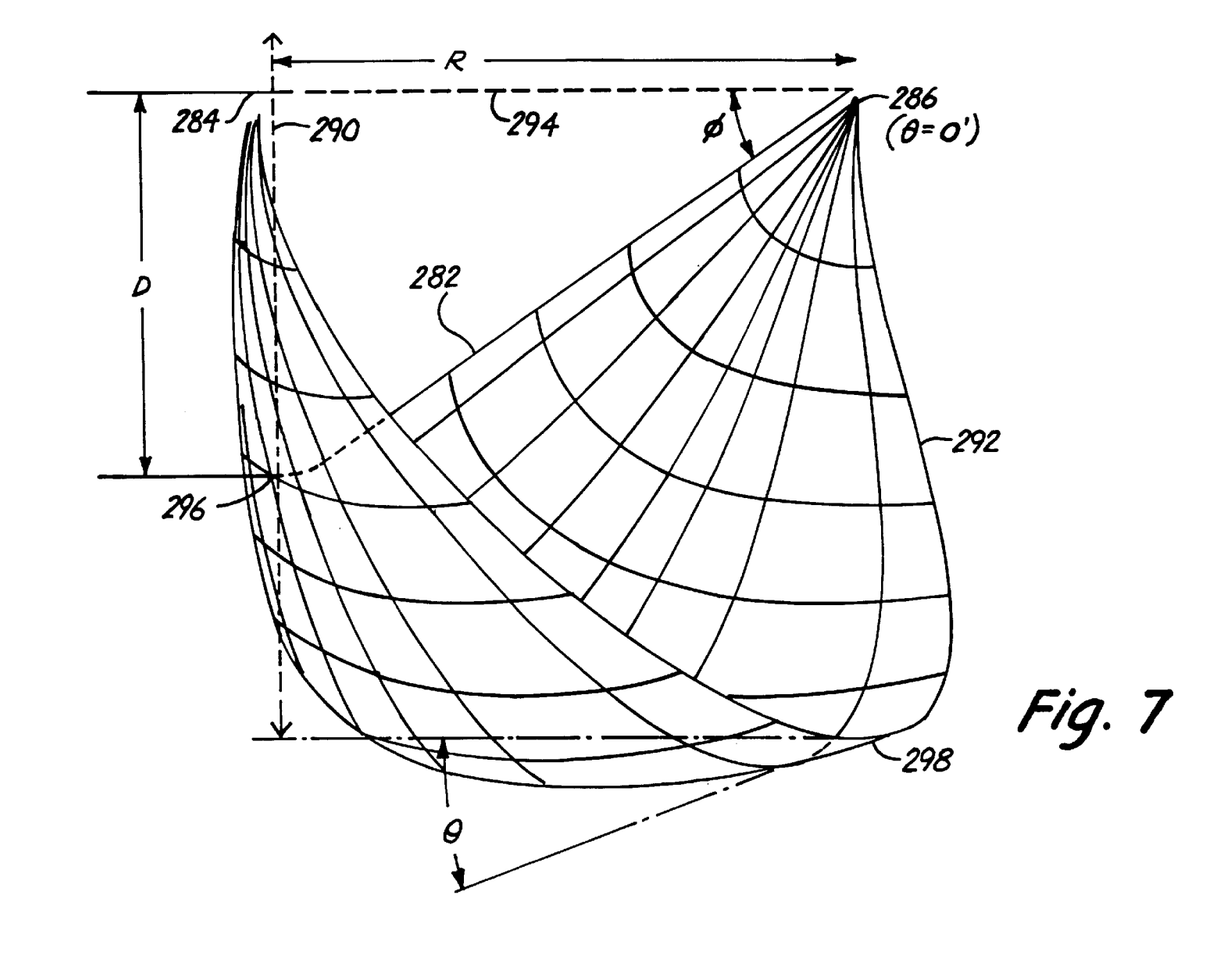
FIG. 7 is a perspective view of the leaflet of FIG. 6 wherein the leaflet is in an orientation corresponding to a closed configuration.

A leaflet in an open configuration separated from the support structure is shown in FIG. 6. The corresponding leaflet in a closed configuration is shown in FIG. 7. The leaflet has a coaptation depth D, as noted in FIG. 7. As shown in FIG. 6, leaflet 280 has a free edge 282 with a length F. Free edge length F is the distance along free edge 282 between attachment points 284, 286. In preferred embodiments, F is at least about 2.05 times the valve radius, preferably about 2.1 to about 2.6, and more preferably from about 2.2 to about 2.5 times the valve radius. The valve radius is the radius of the valve orifice.

For valve designs generally, when the leaflet free edge is greater than twice the valve radius, free edge 282 of leaflet 280 in the closed configuration lies below the plane perpendicular to the valve axis 290 through attachment points, 284, 286 of free edge 282, where free edge 282 meets the support structure and attached edge 292. In contrast, if the free edges of the leaflets have a length approximately twice the valve radius, the leaflets meet in the commissure plane 294 perpendicular to valve axis 290 through attachment points 284, 286 since the center of the free edge must be along the axis of the valve. Referring to FIG. 7, if the length of free edge 282 is longer than twice the valve radius, free edge 282 makes an angle $\phi$ relative to the plane through attachment points 284, 286.

The shape of the valve leaflet, especially in its closed position, is influenced by the valve height and leaflet length. The valve height is related to the valve profile. The valve profile is equal to the valve height plus the extent of the commissure supports beyond the attachment point of the leaflets, if any, and the extent of the base of the support structure at which the valve is attached to the annulus. A valve with too high of a profile may interfere with and possibly cause damage to anatomical structures following implantation. However, a valve with too low of a profile may not be able to sustain the back pressure. In preferred embodiments, a valve height has a value from about one times the valve radius to about 2 times the valve radius, and generally from about 1.2 times the valve radius to about 1.8 times the valve radius.

Referring to FIG. 6, the length L of leaflet 280 is the distance from center of the free edge 282 at coaptation point 296 to the middle 298 of the scallop along attached edge 292. In the closed configuration, length L determines the amount of curvature of the valve leaflet. This degree of curvature affects the stresses in the leaflet. If length L is larger for a selected attached edge configuration, leaflet 280 has greater curvature in the radial direction in the closed configuration since the distance between the attached leaflet edge at point 298 from which L is measured to the coaptation point 296 of free edge 282 is determined by the coaptation depth, see FIG. 7.

The leaflet length preferably is at least about the valve height plus an additional length for coaptation. For leaflets with any relaxed configuration, it is desirable for the leaflet length to be larger than the valve height such that in the closed position, the leaflet can form a desired attachment angle with a smooth bowing profile to distribute stresses effectively. In some preferred embodiments, the leaflet length is greater than about the valve height plus one millimeter (mm) and generally from about the valve height plus 1.5 mm to about 1.2 times the valve height plus 2 mm.

Generally, polymer valves have been designed to have a slope at the attached edge relative to a plane normal to the valve axis and are directed toward the outflow edge of the valve. Thus, at the attached edge, the valve begins immediately to slope toward the outflow end of the valve. However, reduced stresses in the leaflet can be obtained if the leaflet forms an angle with the support structure at the attached edge that points initially toward the inflow end of the valve rather than the outflow end of the valve. Thus, an area of the leaflet is located on the inflow side of a plane passing through the lowest points on the scallops. Since the overall orientation of the leaflet has the free edge toward the outflow end of the valve, the leaflet curves from the initial orientation at the inflow edge to reach the free edge. This curvature provides the leaflet with greater ability to distribute stresses away from localized points. This area of the leaflet on the inflow side of the plane through the lowest scallop points reduces the highest stresses experienced at the commissures.

Figures 8, 9, 12A:
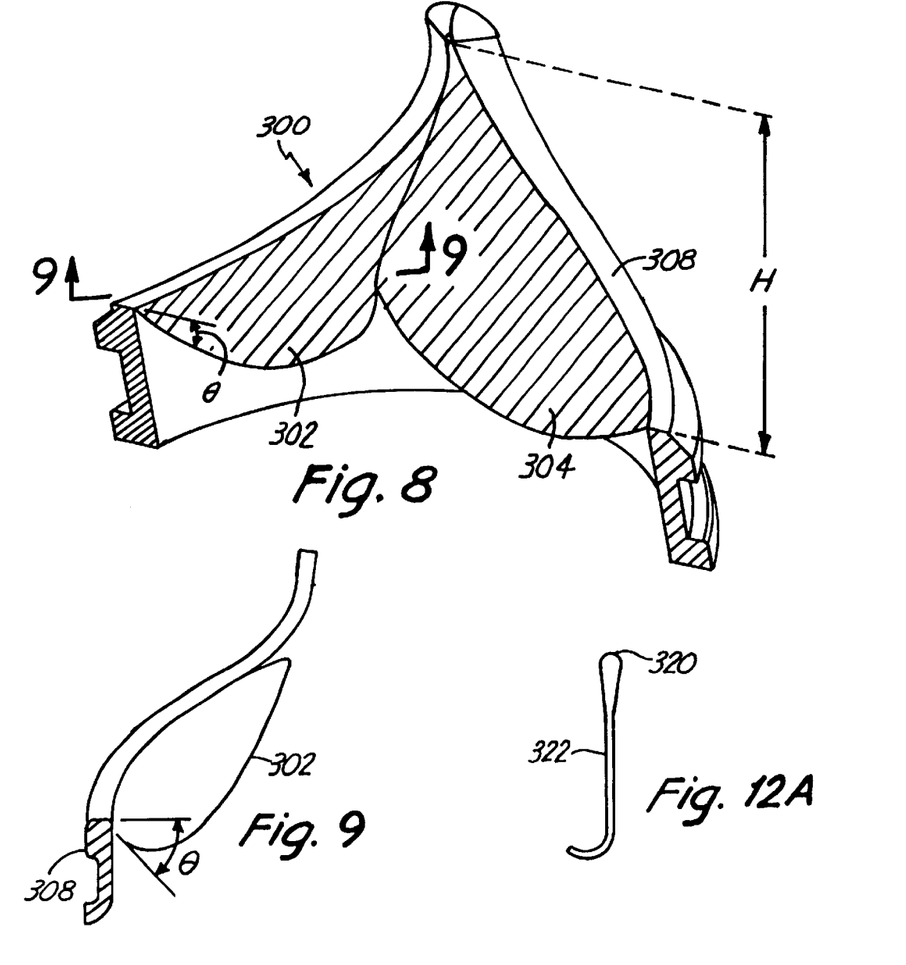
FIG. 8 is a cut away perspective view of a heart valve prosthesis with polymer leaflet, in which the polymer leaflets attach to the support structure at an angle toward the inflow end of the valve.
FIG. 9 is a sectional view of the valve in FIG. 8, where the section is taken along line 9—9.
FIG. 12A is a sectional view of one embodiment of a reinforced polymer leaflet with a thickening of the leaflet at the coaptation edge, the cross section being taken through the center of the leaflet.

The curvature due to the angle "$\Theta$" between the leaflet and a plane normal to the valve axis at the attached edge of the leaflet is shown schematically in FIG. 8. A portion of a complete valve 300 is removed in FIG. 8 to show the attachment of leaflets 302, 304 to support structure 308. A cross section of leaflet 302 is shown in FIG. 9. Attachment angle $\Theta$ is clearly shown in FIG. 9. In preferred embodiments, $\Theta$ is at least about 5°, generally from about 5° to about 85°, preferably from about 10° to about 60° and more preferably from about 10° to about 50°.

Figure 10:
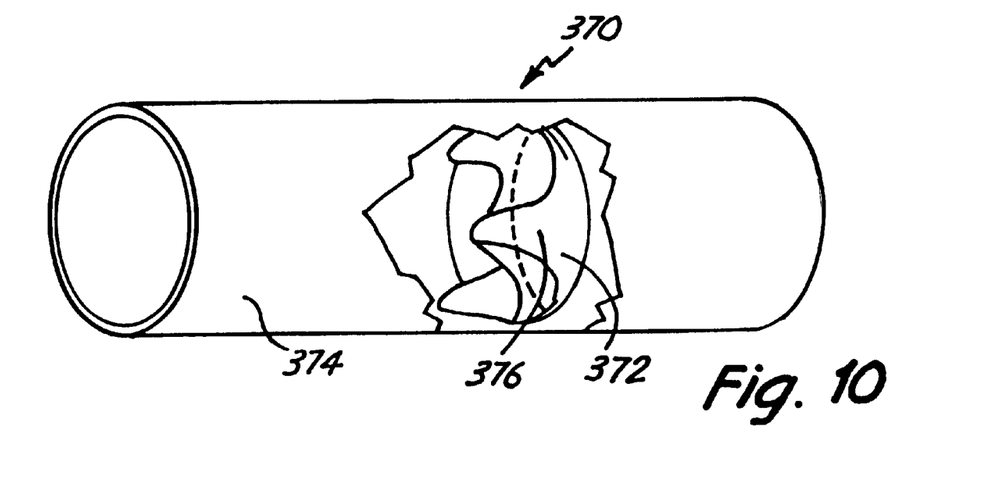
FIG. 10 is a cut away perspective view of a vascular prosthesis incorporating a valve having polymer leaflets in which a portion of the prosthesis has been removed to expose the valve.

The valve prosthesis can be incorporated into a graft for replacement of a venous valve or for the replacement of an aortic or pulmonary heart valve. A valved prosthesis 370 is shown in a fragmentary view in FIG. 10. Prosthesis 370 includes a three-leaflet polymer valve 372 in a conduit 374. Support structure/stent 376 can be rigid or flexible, with corresponding appropriate attachment to conduit 374. For example, if support structure/stent 376 is flexible, the support structure is attached along its outflow edge to conduit 374 for support. Conduit 374 can be made from natural materials, such as fixed bovine pericardium, or synthetic materials, such as polymers, for example, polyesters.

Figure 11:
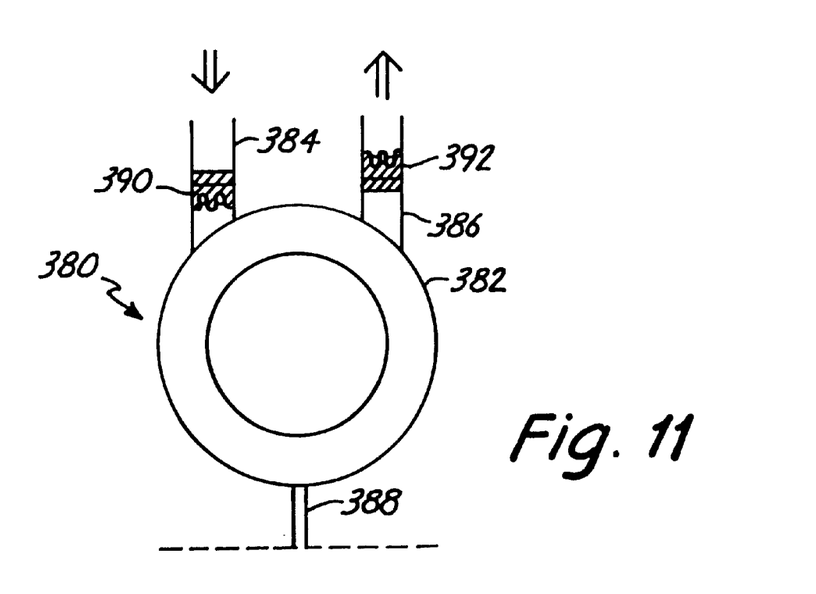
FIG. 11 is a fragmentary side view of a left ventricular assist device with polymer valves, in which the sides of the inflow and outflow tubes have been cut away to expose the inflow and outflow valves.

In addition, polymer valves, as described herein, can be incorporated into a left ventricular assist device 380, as shown in FIG. 11. Left ventricular assist devices are implanted devices generally used to maintain the ventricular pumping function of a patient with a damaged or diseased heart awaiting a heart transplant. Left ventricular assist device 380 includes a drive unit 382, an inflow tube 384, an outflow tube 386 and connection 388. Drive unit 382 includes a pump to provide pulsatile flow from inflow tube 384 to outflow tube 386. Connection 388 provides for electrical or pneumatic control signals to be directed to the drive unit from a controller and power supply, generally external to the patient. Inflow tube 384 includes an inflow valve 390, and outflow tube 386 includes an outflow valve 392. Arrows depict the direction of blood flow through inflow tube 384 and outflow tube 386 as controlled by valves 390, 392. Either one or both of inflow valve 390 and outflow valve 392 can be a polymer valve as described herein.

Material

In general, all of the valves of interest should be constructed from biocompatible materials. Even for valves that are not implanted into a patient, it is desirable for the materials to be biocompatible if they contact a patient's blood or other body fluids. Preferred materials generally depend on the desired mechanical properties of the valve component. Specifically, the nature of preferred materials for the support structure depends on whether or not the support structure is intended to be rigid. The materials and design of the leaflets are selected to achieve desired levels of longevity, tear resistance and mechanical performance.

For any of the prosthetic valve embodiments, if the support structure/stent is formed from a rigid material that supports the leaflets, suitable rigid materials include, for example, rigid polymers, metals, ceramics, carbon materials and combinations thereof. Suitable rigid polymers include, for example, polyacetals, such as Delrin® and Celcon®, polysulfones, polyethersulfones, polyarylsulfones, polyetherether-ketones, and polyetherimides. Suitable metals include biocompatible metals, such as, stainless steel, titanium, titanium alloys, cobalt alloys, such as Elgiloy®, a cobalt-chromium-nickel alloy, and MP35N, a nickel-cobalt-chromium-molybdenum alloy, and Nitinol, a nickel-titanium alloy. Heart valve stents made from spring metals, such as Elgiloy®, exhibit good mechanical properties, such as strength and fatigue endurance, and can have a smaller cross-section than corresponding polymer stents. Composite metal/polymer heart valve stents are described in copending and commonly assigned U.S. patent application Ser. No. 09/475,721 to Reimink et al., entitled "MEDICAL DEVICES WITH POLYMER/INORGANIC SUBSTRATE COMPOSITES," incorporated herein by reference. In addition, stents can be produced from ceramic materials, such as pyrolytic carbon, silicon carbides or metal carbides, hydroxyapatite and alumina. Suitable stents can also be produced from carbons such as graphite.

Support structures that are flexible can be produced, for example, from flexible polymers or metals. Suitable flexible polymers include, for example, polyurethanes, polydimethyl siloxane and polytetrafluoroethylene. Flexible support structures generally can be produced from the same flexible polymer as the leaflets, a different flexible polymer or a combination thereof. To form the support structure, the flexible polymer can be formed into a sheet, woven into a fabric or produced by a variety of other approaches including dip coating, as described further below.

Suitable flexible polymers for support structures also include resorbable polymers, such as, dextran, hydroxyethyl starch, derivatives of gelatine, polyvinylpyrrolidone, poly [N-(2-hydroxylpropyl) methacrylamide], polyglycols, polyesters, poly (orthoesters), poly(ester amides), and polyanhydrides. Resorbable polyesters include, for example, poly (hydroxy acids) and copolymers thereof, poly($\epsilon$-caprolactone), poly (dimethyl glycolic acid), and poly (hydroxy butyrate). Preferred resorbable polymers include, for example, D, L-polylactic acid, L-polylactic acid, poly (glycolic acid), and copolymers of L-lactic acid, D-lactic acid and glycolic acid. The formation of heart valve stents from resorbable polymers is described further in U.S. Pat. No. 5,728,152 to Mirsch II et al., entitled "Bioresorbable Heart Valve Support," incorporated herein by reference. Resorbable polymers can be used for embodiments in which natural structures would be expected to grow as support for the leaflets as a replacement for the rigid stent.

A sewing cuff, if present, can be produced from natural material, synthetic material combinations thereof. Suitable natural materials for sewing cuff 116 include, for example, fixed/crosslinked tissue, such as bovine or porcine pericardial tissue. Crosslinking of tissue provides mechanical stabilization, for example, by preventing enzymatic degradation of the tissue. Crosslinking of tissue also removes antigenic sites that could result in the patient's rejection of the bioprosthesis. Glutaraldehyde or formaldehyde typically is used for fixation, but other fixatives can be used, such as epoxides, genipin, polyimides and other difunctional aldehydes.

Suitable synthetic materials for sewing cuff 116 include flexible polymers, generally woven into a fabric. Preferred materials include, for example, polyesters, or polytetrafluoroethylene. Fabric sewing cuffs can include antimicrobial metals or other antimicrobial agents to reduce the incidence of infection following implantation of the prosthesis into the patient.

Suitable polymeric materials for formation into the leaflets include, for example, synthetic polymers as well as purified biological polymers and combinations thereof. Flexible polymers include elastomers and other polymers that can sustain significant flexure, bending, twisting, wear and/or deformation without structural failure. Preferred polymers are biocompatible. In preferred embodiments of flexible leaflets, the polymer leaflets generally have a thickness from about 50 microns to about 1000 microns and more preferably from about 100 microns to about 300 microns.

Appropriate synthetic polymers include, without limitation, polyamides (e.g., nylon), polyesters, polyacrylates, vinyl polymers (e.g., polyolefins, polyethylene, polytetrafluoroethylene or other halogenated polymers, polypropylene, ethylene-propylene copolymers, ethylene-propylene-diene monomer copolymer (EPDM) and polyvinylchloride), polycarbonates, polyacetals (e.g., Delrin®), polyurethanes, polysiloxanes, cellulose acetates, ethylene vinyl acetates, polysulfones, nitrocelluloses, derivatives thereof, similar copolymers, and mixtures thereof. Particularly preferred flexible polymer materials for the formation of flexible polymer heart valve leaflets include, for example, polyurethanes, polydimethyl siloxanes, polytetrafluoroethylenes, derivatives thereof and mixtures thereof.

A flexible polymer used to form the leaflets of heart valve prostheses is preferably a polymer that has sufficient durability to withstand the repeated cycling required for replacement heart valve use. For a human patient, the valve must cycle about 40 million times each year, and the valve ideally remains functional over the remaining natural expected lifetime of the patient. Current tissue valves may require replacement following about 400 million to about 600 million cycles. Therefore, the polymer substrate preferably can withstand at least about 400 million cycles and more preferably can withstand more than about 600 million cycles without significant structural deterioration. Polyurethanes and silicone polymers are particularly preferred for achieving these performance requirements.

The polymer leaflets can include one or more reinforcements to strengthen the leaflet and/or to make the leaflet more tear resistant. The reinforcement can be formed as a thickening of the flexible polymer or as an additional composition bonded to the flexible polymer forming the body of the leaflet, with or without thickening the leaflet. The reinforcement can be localized or can extend over a significant portion of the leaflet area.

Figure 12B:
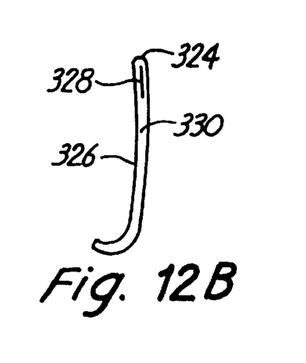
FIG. 12B is a sectional view of an alternative embodiment of a reinforced polymer leaflet with a reinforcing member near the free edge of the leaflet, the cross section being taken through the center of the leaflet.
Figure 12C:
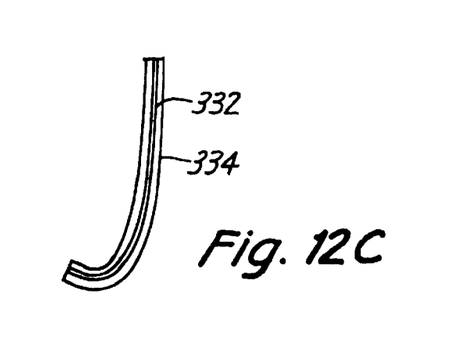
FIG. 12C is a sectional view of an alternative embodiment of a reinforced polymer leaflet with a reinforcing layer, the cross section being taken through the center of the leaflet.

In some preferred embodiments, the free edge of the leaflet is reinforced. Referring to FIG. 12A, free edge 320 of leaflet 322 is thickened to reduce the possibility of tearing or other damage of the free edge. Referring to FIG. 12B, free edge 324 of leaflet 326 includes a reinforcing member 328 with a different composition than body 330 of the leaflet. The reinforcing member may or may not result in a thickening of the free edge relative to the body of the leaflet. If the free edge has a local reinforcement as shown in FIGS. 12A and 12B, additional reinforcements can also be included away from the free edge. Referring to FIG. 12C, a reinforcing member 332 is located throughout the body of leaflet 334. Reinforcing member 332 generally has a different composition than the flexible polymer comprising the remainder of the body of the leaflet.

Reinforcing members preferably are formed from polymer films, perforated polymer films or fabrics. The reinforcing members preferably are relatively flexible and generally have a greater strength than the flexible polymer forming the remainder of the leaflet body. A variety of other reinforcement structures and compositions can be used. Polymer leaflet reinforcements are described further in copending and commonly assigned U.S. patent application, Ser. No.

09/666,823 to Woo et al., entitled "Valved Prostheses With Reinforced Polymer Leaflets," incorporated herein by reference. If the leaflets are formed by dip coating a mandrel, the mandrel can have a groove adjacent to the sharp edge along the surface corresponding to the leaflet free edge to provide for additional thickening along the free edge of the leaflet.

Formation of Valved Prostheses

The leaflets can be formed separate from the support structure, or the leaflets can be formed directly in association with the support structure. If the leaflets are formed separate from the support structure, they can be attached to the support structure by an approach suitable for the particular materials of the components. For example, polymer leaflets can be connected to suitable support structures by heat bonding, suture, adhesive bonding or the like. The leaflets can be formed in direct association with the support structure whether or not the support is formed from the same material. If the leaflets are formed directly in association with the support structure, the support can be incorporated into the process for leaflet formation, as described below.

The leaflets can be formed from the selected polymer by molding, weaving, extruding, dip coating or casting the polymer into appropriate forms. Molding processes can be performed with or without inclusion of a separate support structure/stent within the mold. Preferred methods include casting and dip coating.

To perform dip coating, a mandrel is dipped into a solvent solution of the desired polymer or into a heated polymer melt. When the leaflets are formed on a mandrel, the shape of the mandrel corresponds to the relaxed state of the leaflets since the polymer forms on the mandrel from a liquid without the application of any stresses to the polymer. The mandrel is machined to have the desired shape of the polymer leaflet. In particular, the improved features relating to the leaflet size and shape can be introduced into the leaflet structure by machining the corresponding characteristics into onto the mandrel surface.

A support structure/stent can be placed over the mandrel prior to dip coating to obtain a coating directly over the support structure. Alternatively, a support structure can be formed on the mandrel from the same polymer as the leaflets during the dip coating process. In other alternative embodiments, the leaflets can be associated with the support structure/stent following removal of the leaflets from the mandrel.

The leaflets and, if present, support structures are removed from the mandrel following completion of the coating process. The coating thickness can be varied by changing the temperature of the melt and/or polymer concentration of the solution. Upon cooling and/or evaporation of the solvent, the polymer structure is formed on the mandrel. Multiple dipping steps can be used if desired.

To form a leaflet reinforcement in a molding process, the mold can be altered to provide a thickened portion of the leaflet at the reinforcement. Alternatively, a reinforcement material can be placed in the mold at the location of the reinforcement such that the polymer forms the leaflet around the reinforcement material. In a dip coating process, the shape of the mandrel can be varied to provide a thickened edge, or the free edge can be dipped additional times to provide a thickened portion at that edge. Alternatively, a reinforcement material can be placed along the mandrel either at the start of the dip coating process or after an initial polymer coating has been formed.

Dip coating approaches for the formation of polymer leaflets can be performed using an improved mandrel design that yields polymer leaflets with more consistent properties. In particular, the mandrel can include a sharp edge at the top of the mandrel positioned at the desired location of the free edge of the leaflet. If the polymer is separated along a sharp edge, the free edge of the leaflets is defined reproducibly by the mandrel sharp edge. In contrast, approaches in which the top of the leaflets are cut according to predetermined measurements result in variation in the precise position of the leaflet free edge due to limitation in measurement and due to potential stretching of the polymer during the cutting process. These improved mandrel designs with a sharp edge are described further in copending and commonly assigned U.S. patent application Ser. No. 09/724,007 to Kurk et al., entitled "Polymer Valve Prostheses by Dip Coating," incorporated herein by reference.

After the leaflets are formed, additional processing steps may be needed to complete the production of the prosthesis. First, if the leaflets were not formed directly in association with the support structure/stent, the leaflets are connected to the support structure. Any additional structures, such as a sewing cuff, are connected to the support structure. Sewing cuffs and the like generally are added at or near the inflow edge. If the valve is incorporated into a conduit, the conduit can be connected to or formed around the valve such that the valve is securely connected to the conduit. Suture, staples, adhesive, and other fastening mechanisms and combinations thereof can be used to connect the support structures to the other components.

Packaging Distribution and Use

For distribution, the medical devices are placed in sealed and sterile containers. The containers can be dated such that the date reflects the maximum advisable storage time, if components of the medical device should not be stored indefinitely. The containers are packaged along with instructions for the proper use and/or implantation of the medical device and along with other appropriate and/or required labeling. The containers are distributed to health care professionals for use in appropriate medical procedures, such as implantation of a prosthesis and the like. Heart valve prostheses and valved vascular prostheses can be implanted, for example, using standard surgical procedures.

The embodiments above are intended to be illustrative and not limiting. Additional embodiments are within the claims. Although the present invention has been described with reference to preferred embodiments, workers skilled in the art will recognize that changes may be made in form and detail without departing from the spirit and scope of the invention.

What is claimed is:

1. A valved prosthesis comprising a support structure and a plurality of flexible polymer leaflets connected to the support structure, the support structure having a plurality of commissure supports and scallops between the commissure supports, the valve having a relaxed state with a lumen that is at least 10 percent of the fully open lumen and, at a point along the scallops closest to the inflow edge, the flexible polymer leaflets connecting to the support structure at an angle toward the inflow edge from about 5 degrees to about 85 degrees relative to a plane normal to the valve axis.

2. The valved prosthesis of claim 1 wherein the support structure comprises a rigid stent.

3. The valved prosthesis of claim 1 wherein the support structure comprises a flexible material.

4. The valved prosthesis of claim 3 wherein the flexible material comprises a polymer composition found in the flexible polymer leaflet.

5. The valved prosthesis of claim 1 wherein the flexible polymer leaflets comprise a reinforcement.

6. The valved prosthesis of claim 1 wherein the flexible polymer leaflets have a reinforced free edge.

7. The valved prosthesis of claim 1 wherein the flexible polymer leaflets connect to the support structure at an angle toward the inflow edge from about 10 degrees to about 60 degrees.

8. The valved prosthesis of claim 1 wherein the flexible polymer leaflets connect to the support structure at an angle toward the inflow edge from about 10 degrees to about 50 degrees.

9. The valved prosthesis of claim 1 wherein the valve has a relaxed state with a lumen that is at least about 90 percent of the full open lumen.

10. The valved prosthesis of claim 1 wherein the valve has a relaxed state with a lumen that is between about 50 percent and about 80 percent of the full open lumen.

11. The valved prosthesis of claim 1 wherein the plurality of flexible polymer leaflets is three leaflets.

12. The valved prosthesis of claim 1 wherein the flexible polymer leaflets comprise a polymer selected from the group consisting of polyurethanes, silicones, polydimethyl siloxane, polytetrafluoroethylene, derivatives thereof and mixtures thereof.

13. A valved prosthesis comprising a support structure and at least three flexible polymer leaflets connected to the support structure, the support structure having a plurality of commissure supports and scallops between the commissure supports and the flexible polymer leaflets having a coaptation depth from about 0.3 times the valve radius to about 0.8 times the valve radius.

14. The valved prosthesis of claim 13 wherein the leaflets have reinforced free edges.

15. The valved prosthesis of claim 13 wherein the leaflets have a coaptation depth from about 0.3 times the valve radius to about 0.6 times the valve radius.

16. The valved prosthesis of claim 13 wherein the valve has a relaxed state with a lumen that is at least about 90 percent of the full open lumen.

17. The valved prosthesis of claim 13 wherein the valve has a relaxed state with a lumen that is between about 50 percent and about 80 percent of the full open lumen.

18. The valved prosthesis of claim 13 wherein the valve has a relaxed state with a lumen that is no more than about 10 percent of the full open lumen.

19. The valved prosthesis of claim 13 wherein the support structure comprises a rigid stent.

20. The valved prosthesis of claim 13 wherein the support structure comprises a flexible material.

21. A valved prosthesis comprising a support structure and a plurality of flexible polymer leaflets, the support structure having a plurality of commissure supports and scallops between the commissure supports and the flexible polymer leaflets form a valve with a valve height from about one times the valve radius to about 2 times the valve radius and having leaflet lengths at least about 1 millimeter greater than the valve height.

22. The valved prosthesis of claim 21 wherein the plurality of leaflets is three leaflets.

23. The valved prosthesis of claim 21 wherein the leaflets have a reinforced free edge.

24. The valved prosthesis of claim 21 wherein the leaflets have a leaflet length from about 1.5 millimeters greater than the valve height to about 1.2 times the valve height plus 2 millimeters.

25. The valved prosthesis of claim 21 wherein the valve height is from about 1.2 times the valve radius to about 1.8 times the valve radius.

26. The valved prosthesis of claim 21 wherein the valve has a relaxed state with a lumen that is at least about 90 percent of the full open lumen.

27. The valved prosthesis of claim 21 wherein the valve has a relaxed state with a lumen that is between about 50 percent and about 80 percent of the full open lumen.

28. The valved prosthesis of claim 21 wherein the valve has a relaxed state with a lumen that is no more than about 10 percent of the full open lumen.

29. The valved prosthesis of claim 21 wherein the flexible polymer leaflets connect to the support structure at an angle toward the inflow edge from about 5 degrees to about 85 degrees relative to a plane normal to the valve axis.

30. The valved prosthesis of claim 29 wherein the flexible polymer leaflets connect to the support structure at an angle toward the inflow edge from about 10 degrees to about 60 degrees.

31. The valved prosthesis of claim 29 wherein the flexible polymer leaflets connect to the support structure at an angle toward the inflow edge from about 10 degrees to about 50 degrees.

32. The valved prosthesis of claim 21 wherein the plurality of leaflets is three leaflets.

* * * * *